(12) United States Patent
Liu et al.

(10) Patent No.: US 11,697,818 B2
(45) Date of Patent: Jul. 11, 2023

(54) PYRUVATE-RESPONSIVE BIOSENSOR, AND CONSTRUCTION METHOD AND USE THEREOF

(71) Applicant: JIANGNAN UNIVERSITY, Wuxi (CN)

(72) Inventors: Long Liu, Wuxi (CN); Jian Chen, Wuxi (CN); Xueqin Lv, Wuxi (CN); Guocheng Du, Wuxi (CN); Jianghua Li, Wuxi (CN); Xianhao Xu, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 156 days.

(21) Appl. No.: 17/133,524

(22) Filed: Dec. 23, 2020

(65) Prior Publication Data

US 2022/0010318 A1    Jan. 13, 2022

(30) Foreign Application Priority Data

Jun. 19, 2020 (CN) .......................... 202010566287.X

(51) Int. Cl.
*C12N 15/75* (2006.01)
*C07K 14/32* (2006.01)

(52) U.S. Cl.
CPC .............. *C12N 15/75* (2013.01); *C07K 14/32* (2013.01); *C12N 2830/002* (2013.01)

(58) Field of Classification Search
None
See application file for complete search history.

(56) References Cited

FOREIGN PATENT DOCUMENTS

CN    110724702 A  *  1/2020

* cited by examiner

*Primary Examiner* — Suzanne M Noakes
(74) *Attorney, Agent, or Firm* — SZDC Law P.C.

(57) ABSTRACT

The present invention provides a pyruvate-responsive biosensor and a construction method and use thereof. In the present invention, pyruvate-responsive biosensors with different dynamic ranges are successfully constructed by optimizing the PdhR binding sequence inserted on the P43 promoter and optimizing the insertion site, wherein the minimum increase in dynamic range is by 0.6 time, and the maximum increase is by 30.7 times. The pyruvate-responsive biosensors are useful in the precise control of the expression of each gene in the cell. Since pyruvate is a key metabolite of central carbon in the cells, these biosensors are capable of dynamically regulating the expression level of intracellular genes according to changes in the content of pyruvate in the cells, thereby achieving the dynamic control of intracellular metabolic flux. The pyruvate biosensor obtained in the present invention has a good specificity, and a response range to pyruvate of 10-35 nmol/g DCW.

6 Claims, 6 Drawing Sheets

Specification includes a Sequence Listing.

PdhR Box: ATTGGTNNACCAAT

Box1: ATTGGTAAGACCAAT
Box2: ATTGGTATGACCAAT
Box3: ATTGGTAATACCAAT
Box4: ATTGGTTAAACCAAT
Box5: ATTGGTATTACCAAT
Box6: ATTGGTTTAACCAAT
Box7: ATTGGTACTACCAAT
Box8: ATTGGTAGTACCAAT
Box9: ATTGGTTGAACCAAT
Box10: ATTGGTGACACCAAT

PYRUVATE-RESPONSIVE BIOSENSOR, AND CONSTRUCTION METHOD AND USE THEREOF

This application claims priority to Chinese Patent Application No. 202010566287.X, filed on Jun. 19, 2020, which is incorporated by reference for all purposes as if fully set forth herein.

FIELD OF THE INVENTION

The present invention relates to the technical field of metabolic engineering, and more particularly to a pyruvate-responsive biosensor and a construction method and use thereof.

DESCRIPTION OF THE RELATED ART

The metabolic engineering mainly aims to efficiently synthesize required chemicals, such as drugs, materials, biofuels, fine chemicals and functional nutrients, with microorganisms as hosts and biomass as raw materials. However, the traditional metabolic engineering techniques (overexpression of related genes in the product synthesis pathways, knockout of competitive pathways, and optimization of cofactors, etc.) often lead to problems such as imbalanced intracellular metabolic flux, low raw material utilization, and accumulation of toxic metabolites. Therefore, it is difficult to maximize the titer and productivity of a compound. In addition, although traditional mutagenesis breeding methods can quickly generate large number of mutant strains, the existing screening methods have difficulty to quickly obtain a high-producing target strain from these mutant strains. For example, the high-performance liquid chromatography-mass spectrometry technology is high in cost and low in screening throughput. Therefore, there is an urgent need to find an efficient technology or method for metabolic engineering of microorganisms.

With the development of synthetic biology, biosensors are widely used in metabolic engineering, environmental monitoring, and regular targeted therapy. Biosensors are a class of biologically derived sensing elements that can recognize a specific substance and finally convert the input signal into an output signal. According to the type of substance recognized by a biosensor, biosensors can be divided into biosensors that respond to environmental signals, extracellular compounds and intracellular compounds. Biosensors generally have a ligand sensing element that responds to signals and an executing element that enables signal output. At present, most biosensors are obtained by modifying the transcriptional regulators or riboswitches. Transcriptional regulators and riboswitches are a class of proteins or RNAs in an organism that can respond to specific signals and regulate the expression of related genes in the cell. Riboswitches have the advantages of simple structure and obvious regulatory effects, but they often have low specificity and poor stability. Although the transcriptional regulators are more complex in structure, they have higher specificity and better stability. Therefore, the transcriptional regulators are more suitable for use in the construction and design of highly specific biosensors. Biosensors can be used to design artificial gene circuits, dynamically control the intracellular metabolic flux, and balance the cell growth and product synthesis, thus achieving the efficient synthesis of a product. In addition, compared with the traditional metabolite detection methods, the biosensors have higher sensitivity and more convenient detection means, thus being applicable to the high-throughput screening of high-producing mutant strains. Therefore, the biosensors are currently widely used in the dynamic control of microbial metabolic networks, and the high-throughput screening and directed evolution of high-producing strains of target products.

Pyruvate is a key central metabolite that connects the glycolytic pathway and the tricarboxylic acid cycle in organisms. On the one hand, it provides cells with the carbon skeleton to synthesize other compounds, and on the other hand, it flows into the tricarboxylic acid cycle to provide cells with the necessary reducing power and energy. Therefore, the intracellular pyruvate level is not only an important detection target for the occurrence of diseases in organisms, but also an important regulatory node for microbial metabolic engineering. Therefore, the constructed pyruvate-responsive biosensor is useful in the monitoring of intracellular pyruvate level and the dynamic control of microbial central carbon metabolism to achieve efficient synthesis of a target product.

At present, some pyruvate biosensors have been designed based on the naturally occurring pyruvate-responsive transcriptional regulator PdhR in China and other countries. In 2014, Barros et al. successfully constructed a pyruvate-responsive biosensor based on the fluorescence resonance energy transfer technology and PdhR, which is useful in the detection of intracellular pyruvate concentration. In 2019, Zhang Dawei et al. of the Tianjin Institute of Industrial Biotechnology, Chinese Academy of Sciences published a patent in which another pyruvate biosensor is successfully obtained based on PdhR, the promoter $P_{ap}$, and the reporter gene gfp, and a PdhR mutant that can respond to different concentrations of pyruvate is obtained by constructing a PdhR mutant library, where the mutant can be used in the high-throughput screening of mutants highly producing pyruvate and precursor compounds thereof.

The pyruvate-responsive biosensor constructed by Barros et al. does not have the function of regulating gene expression, so it can only be used as a reporter system to monitor the concentration of intracellular pyruvate, and cannot be used for the metabolic engineering of a strain. The pyruvate-responsive sensor constructed by Zhang Dawei et al. is mainly used in the high-throughput screening of pyruvate and precursor compounds thereof. By simply screening PdhR mutants, a pyruvate biosensor that can respond to different concentrations of pyruvate have been obtained. This sensor is suitable for the high-throughput screening of mutant strains producing pyruvate and precursor compounds thereof. However, other necessary components are not modified in this sensor, so the sensor has difficulty in achieving the precise control of the expression of multiple metabolic pathways in a complex metabolic network, and thus is difficult to be used in the dynamic control of a bacterial metabolic network.

SUMMARY OF THE INVENTION

To solve the above technical problems, the present invention intends to construct a series of pyruvate-responsive biosensors with different dynamic ranges in *Bacillus subtilis* based on PdhR, the promoter P43, and the reporter gene egfp. These sensors are useful in the precise control of expression levels of genes in a strain, and thus useful in the dynamic control of the central metabolic network of the strain.

A first object of the present invention is to provide a pyruvate-responsive biosensor, which comprises a PdhR gene, a P43 promoter, and a PdhR binding sequence inserted on the P43 promoter.

Preferably, the nucleotide sequence of the PdhR binding sequence is as shown in SEQ ID NO:1, SEQ ID NO:2, SEQ ID NO:3 or SEQ ID NO:5.

Preferably, the insertion site of the PdhR binding sequence on the P43 promoter is the +1 site, the 5th site upstream of the +1 site or one of the 1st to 11th sites downstream of the +1 site.

In the present invention, the P43 sequence is ccaaggacgctgccgccggggctgtttgcgttttgccgtgatttcgtgtatcattggtttacttatttttttgccaaagctgtaatggctgaa aattcttacatttattttacatttttagaaatgggc$\boxed{\text{gtgaaa}}$aaaagcgcgcgattat$\boxed{\text{ctaaaat}}$ataa$\boxed{\text{a}}$gtgatagcggtaccCTCGA

GAAAAGGAGGAAAAAAA (SEQ ID NO: 13), in which the boxed sequences represent −35 region, −10 region and +1 site respectively.

Preferably, the PdhR gene is integrated into the upstream of the ycgB gene in the *Bacillus subtilis* genome.

Preferably, the nucleotide sequence of the PdhR gene is as shown in SEQ ID NO:11.

Preferably, the biosensor also comprises a reporter gene egfp located downstream of the P43 promoter.

Preferably, the P43 promoter, the PdhR binding sequence and the reporter gene egfp are located on the vector PHT01.

A second object of the present invention is to provide a phase-dependent pyruvate-responsive biosensor. The phase-dependent pyruvate-responsive biosensor comprises a PdhR gene, a phase-dependent promoter and a PdhR binding sequence inserted in the −35 region, −10 region or the +1 site of the phase-dependent promoter, where the phase-dependent promoter is $P_{yteJ}$, $P_{ywjC}$ or $P_{yqfd}$.

A third object of the present invention is to provide use of the pyruvate-responsive biosensor or the phase-dependent pyruvate-responsive biosensor in the metabolic regulation of *Bacillus subtilis*.

Preferably, the use includes constructing a target gene at the downstream of the promoter, to regulate the expression of the target gene through pyruvate.

The present invention has the following beneficial effects.

1. In the present invention, pyruvate-responsive biosensors having different dynamic ranges with a minimum increase of 0.6 time and a maximum increase of 30.7 times are successfully constructed. They can be used for precise control of the expression of each gene in the cell. Since pyruvate is a key metabolite of central carbon in cells, these biosensors can dynamically regulate the expression level of intracellular genes according to changes in the content of pyruvate in the cell, thereby achieving the dynamic control of intracellular metabolic flux.

2. The pyruvate biosensor of the present invention has good specificity, and a response range to pyruvate of 10-35 nmol/g DCW.

3. In the present invention, a phase-dependent pyruvate biosensor is successfully obtained, including a lag-log phase-dependent and a stationary phase-dependent pyruvate-responsive promoter. These phase-dependent pyruvate biosensors are useful in the temporal expression of intracellular genes. For example, for the expression of genes related to the synthesis pathway of toxic metabolites, the stationary phase-dependent pyruvate-responsive promoter can allow the regulated genes to express after the stationary phase, thus avoiding the harmful effect caused by premature accumulation of toxic compounds on cells.

DETAILED DESCRIPTION OF THE PREFERRED EMBODIMENTS

Figure 1:
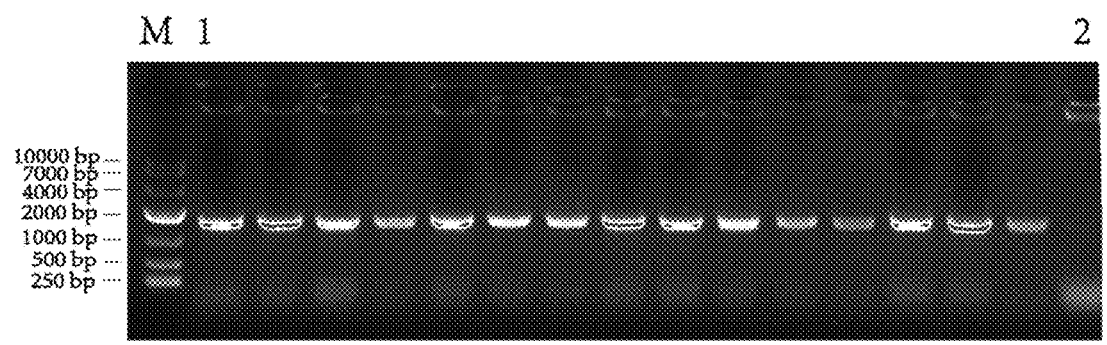
FIG. 1 is an electrophoretogram of nucleic acids for the verification of strain 168-PR.

The present invention will be further described below with reference to the accompanying drawings and specific examples, so that those skilled in the art can better understand and implement the present invention; however, the present invention is not limited thereto.

Detection methods involved:

1. Detection method of intracellular pyruvate level: Pyruvate (PA) content detection kit (article number: BC2205) available from Solarbio is used to detect the intracellular pyruvate content.

2. Detection method for Relative fluorescence intensity: The strain to be determined for the fluorescence intensity is streaked into LB solid medium containing chloramphenicol (5 μg/mL) in a plate. Single colonies are picked up and inoculated into LB liquid medium and incubated at 37° C. and 220 rpm for 12 h. Then the cell suspension is inoculated into 200 μL of LB liquid medium in a 96-well fluorescent microplate in an amount of 2% (V/V), and incubated at 37° C. and 900 rpm. The microplate is removed at different times, and the fluorescence intensity (excitation light: 488 nm, absorption light: 520 nm) and cell density (600 nm) are determined on the Cytation microplate reader (BioTek).

3. Isothermal microcalorimetric titration detection: MicroCal PEAQ-ITC from Malvern is used for isothermal microcalorimetric titration detection of PdhR with pyruvate and a hybrid promoter, respectively. The instrument parameters are default parameters, and the analysis software is the supporting MicroCal PEAQ-ITC Analysis Software.

TABLE 1

Primer sequence

| Names | Sequence |
|---|---|
| P43D-F | CGGTACCATTGGTATGACCAATCTCGAGAAAAGGAGGAAAAAAATGGGTAA (SEQ ID NO: 14) |
| P43D-R | TCTCGAGATTGGTCATACCAATGGTACCGCTATCACTTTATATTTTACATAATCG (SEQ ID NO: 15) |
| P43U-F | ATTGGTATGACCAATCTGTAATGGCTGAAAATTCTTACATTTATTT (SEQ ID NO: 16) |
| P43U-R | TACAGATTGGTCATACCAATCTTTGGCAAAAAATAAGTAAACCAATG (SEQ ID NO: 17) |
| P43M-F | AAAAAATTGGTATGACCAATGCGCGCGATTATGTAAAATATAAAGTGA (SEQ ID NO: 18) |
| P43M-R | ATTGGTCATACCAATTTTTTTTCACGCCCATTTCTAAAAATGT (SEQ ID NO: 19) |
| P43-pdhR-F | GGTAAGAGAGGAATGTACACATGGCCTACAGCAAAATCCGCCAACC (SEQ ID NO: 20) |
| P43-pdhR-R | CCCGTCTAGCCTTGCCCCTAATTCTTTCGTTGCTCCAGACGACGC (SEQ ID NO: 21) |
| pdhR-FF | GATTTGGTTCTTGATCGGGCTTGTCTTTA (SEQ ID NO: 22) |
| pdhR-FR | GTGTGAAATTGTTATCCGCTCTTACTTCATTCTTCCGCTTCCTCCTTTCAA (SEQ ID NO: 23) |
| pdhR-RF | GTCTGGAGCAACGAAAGAATTAGGGGCAAGGCTAGACGGGACTTACC (SEQ ID NO: 24) |
| pdhR-RR | AACGAGTTCACTGACCGGCACACC (SEQ ID NO: 25) |
| Z_PET28F | GCTAGCCATATGGCTGCCGC (SEQ ID NO: 26) |
| Z_PET28R | ATGACTGGTGGACAGCAAATGGG (SEQ ID NO: 27) |
| 28apdhRF | ATTTGCTGTCCACCAGTCATCTAATTCTTTCGTTGCTCCAGACGACGC (SEQ ID NO: 28) |
| 28apdhRR | GCGGCAGCCATATGGCTAGCATGGCCTACAGCAAAATCCGCCAACC (SEQ ID NO: 29) |
| P43DF | ACAGCCATTGAACATACGGTTG (SEQ ID NO: 30) |
| P43DR | TTTTTTTCCTCCTTTTCTCGAGATTGGT (SEQ ID NO: 31) |
| pdhRBox-F1 | CCGCATTGGTAAGACCAATGTACG (SEQ ID NO: 32) |
| pdhRBox-R1 | TACATTGGTTTAACCAATGCGGCC (SEQ ID NO: 33) |
| pdhRBox-F2 | CCGCATTGGTATGACCAATGTACG (SEQ ID NO: 34) |
| pdhRBox-R2 | TACATTGGTCATACCAATGCGGCC (SEQ ID NO: 35) |
| pdhRBox-F3 | CCGCATTGGTAATACCAATGTACG (SEQ ID NO: 36) |
| pdhRBox-R3 | TACATTGGTATTACCAATGCGGCC (SEQ ID NO: 37) |

TABLE 1-continued

Primer sequence

| Names | Sequence |
|---|---|
| pdhRBox-F4 | CCGCATTGGTTAAACCAATGTACG (SEQ ID NO: 38) |
| pdhRBox-R4 | TACATTGGTTTAACCAATGCGGCC (SEQ ID NO: 39) |
| pdhRBox-F5 | CCGCATTGGTATTACCAATGTACG (SEQ ID NO: 40) |
| pdhRBox-R5 | TACATTGGTAATACCAATGCGGCC (SEQ ID NO: 41) |
| pdhRBox-F6 | CCGCATTGGTTTAACCAATGTACG (SEQ ID NO: 42) |
| pdhRBox-R6 | TACATTGGTTAAACCAATGCGGCC (SEQ ID NO: 43) |
| pdhRBox-F7 | CCGCATTGGTACTACCAATGTACG (SEQ ID NO: 44) |
| pdhRBox-R7 | TACATTGGTAGTACCAATGCGGCC (SEQ ID NO: 45) |
| pdhRBox-F8 | CCGCATTGGTAGTACCAATGTACG (SEQ ID NO: 46) |
| pdhRBox-R8 | TACATTGGTACTACCAATGCGGCC (SEQ ID NO: 47) |
| pdhRBox-F9 | CCGCATTGGTTGAACCAATGTACG (SEQ ID NO: 48) |
| pdhRBox-F9 | TACATTGGTTCAACCAATGCGGCC (SEQ ID NO: 49) |
| pdhRBox-F10 | CCGCATTGGTGACACCAATGTACG (SEQ ID NO: 50) |
| dhRBox-R10 | TACATTGGTGTCACCAATGCGGCC (SEQ ID NO: 51) |
| D(-5)F | GTAAAATTGGTAAGACCAATATAAAGTGATAGCGGTACCCTCGAGA (SEQ ID NO: 52) |
| D(-5)R | ATTGGTCTTACCAATTTTACATAATCGCGCGCTTTTTTTC (SEQ ID NO: 53) |
| D1F | ATAAAATTGGTAAGACCAATGTGATAGCGGTACCCTCGAGAAAAG (SEQ ID NO: 54) |
| D1R | CTATCACATTGGTCTTACCAATTTTATATTTTACATAATCGCGCGCTTTTTTT (SEQ ID NO: 55) |
| D2F | ATTGGTCTTACCAATCTTTATATTTTACATAATCGCGCGCTTT (SEQ ID NO: 56) |
| D2R | TAAAGATTGGTAAGACCAATTGATAGCGGTACCCTCGAGAAAAG (SEQ ID NO: 57) |
| D3F | CATTGGTCTTACCAATACTTTATATTTTACATAATCGCGCGCTT (SEQ ID NO: 58) |
| D3R | AAGTATTGGTAAGACCAATGATAGCGGTACCCTCGAGAAAAGG (SEQ ID NO: 59) |
| D4F | AAGTGATTGGTAAGACCAATATAGCGGTACCCTCGAGAAAAGG (SEQ ID NO: 60) |
| D4R | ATTGGTCTTACCAATCACTTTATATTTTACATAATCGCGCGCT (SEQ ID NO: 61) |
| D5F | AGTGAATTGGTAAGACCAATTAGCGGTACCCTCGAGAAAAGGAG (SEQ ID NO: 62) |

TABLE 1-continued

Primer sequence

| Names | Sequence |
|---|---|
| D5R | ATTGGTCTTACCAATTCACTTTATATTTTACATAATCGCGCGCT<br>(SEQ ID NO: 63) |
| D6F | GTGATATTGGTAAGACCAATAGCGGTACCCTCGAGAAAAGGA<br>(SEQ ID NO: 64) |
| D6R | ATTGGTCTTACCAATATCACTTTATATTTTACATAATCGCGCGC<br>(SEQ ID NO: 65) |
| D7F | TGATAATTGGTAAGACCAATGCGGTACCCTCGAGAAAAGGA<br>(SEQ ID NO: 66) |
| D7R | ATTGGTCTTACCAATTATCACTTTATATTTTACATAATCGCGCGCTT<br>(SEQ ID NO: 67) |
| D8F | GATAGATTGGTAAGACCAATCGGTACCCTCGAGAAAAGGAGG<br>(SEQ ID NO: 68) |
| D8R | ATTGGTCTTACCAATCTATCACTTTATATTTTACATAATCGCGCGC<br>(SEQ ID NO: 69) |
| D9F | ATAGCATTGGTAAGACCAATGGTACCCTCGAGAAAAGGAGGAA<br>(SEQ ID NO: 70) |
| D9R | ATTGGTCTTACCAATGCTATCACTTTATATTTTACATAATCGCGCG<br>(SEQ ID NO: 71) |
| D10F | TAGCGATTGGTAAGACCAATGTACCCTCGAGAAAAGGAGGAAAA<br>(SEQ ID NO: 72) |
| D10R | ATTGGTCTTACCAATCGCTATCACTTTATATTTTACATAATCGCGC<br>(SEQ ID NO: 73) |
| D11F | AGCGGATTGGTAAGACCAATTACCCTCGAGAAAAGGAGGAAAAAAAATG<br>(SEQ ID NO: 74) |
| D11R | ATTGGTCTTACCAATCCGCTATCACTTTATATTTTACATAATCGCGC<br>(SEQ ID NO: 75) |
| Z_PHT01-F | ATGGGTAAGGGAGAAGAACTTTTCACT<br>(SEQ ID NO: 76) |
| Z_PHT01-R | ACCACCTATCAGGATCCAGTTGCA<br>(SEQ ID NO: 77) |
| PyteJ-F | GTGCAACTGGATCCTGATAGGTGGTGGTTCACAACGGTAAATCCATGCT<br>(SEQ ID NO: 78) |
| PyteJ-R | TGAAAAGTTCTTCTCCCTTACCCATTTTTTCTCCTCCTTTTTCCTAAACTCTCTCA<br>(SEQ ID NO: 79) |
| Pywjc-F | GTGCAACTGGATCCTGATAGGTGGTTTCCCCAAAATCGGAGCAAGCG<br>(SEQ ID NO: 80) |
| Pywjc-R | TGAAAAGTTCTTCTCCCTTACCCATGATCTTTCTCCTCCATCGATTGTTGTCT<br>(SEQ ID NO: 81) |
| PyqfD-F | GTGCAACTGGATCCTGATAGGTGGTTATCCCTAACCGTATGGAACAGGC<br>(SEQ ID NO: 82) |
| PyqfD-R | TGAAAAGTTCTTCTCCCTTACCCATACAAAAAGAACCCCCTTTCATCTCATAT<br>(SEQ ID NO: 83) |
| PyteJU-F | ATGTTTCAATTGGTCTTACCAATCTTCATGAGAAAGCTCCGGCTTAAC<br>(SEQ ID NO: 84) |
| PyteJU-R | GGTAAGACCAATTGAAACATTTTTCATATTGAATCGTATAATGAGAGAGTTTAGGAA<br>(SEQ ID NO: 85) |
| PyteJD-F | GTATAATTGGTAAGACCAATATGAGAGAGTTTAGGAAAAAGGAGGAGAA<br>(SEQ ID NO: 86) |
| PyteJD-R | ATTGGTCTTACCAATTATACGATTCAATATGAAAAATGTTTCACTTCATGAGAAAGC<br>(SEQ ID NO: 87) |
| PyteJ1-F | GAGAGATTGGTAAGACCAATAGTTTAGGAAAAAGGAGGAGAAAAAAATGGG |

TABLE 1-continued

Primer sequence

| Names | Sequence |
|---|---|
|  | (SEQ ID NO: 88) |
| PyteJ1-R | ATTGGTCTTACCAATCTCTCATTATACGATTCAATATGAAAAATGTTTCACT<br>(SEQ ID NO: 89) |
| PywjcU-F | AAAATATTGGTAAGACCAATAGGTTTACGACTTGTCAGCTTTGGG<br>(SEQ ID NO: 90) |
| PywjcU-R | ATTGGTCTTACCAATATTTTTGCACATTTATGACTTCCATTGCA<br>(SEQ ID NO: 91) |
| PywjcD-F | ATTGGTAAGACCAATTTAGGCTATATAAGACAACAATCGATGGAGG<br>(SEQ ID NO: 92) |
| PywjcD-R | CCTAAATTGGTCTTACCAATGTTCCCAAAGCTGACAAGTCGTAAAC<br>(SEQ ID NO: 93) |
| Pywjc1-F | TATATATTGGTAAGACCAATAAGACAACAATCGATGGAGGAGAAAG<br>(SEQ ID NO: 94) |
| Pywjc1-R | ATTGGTCTTACCAATATATAGCCTAAGTTCCCAAAGCTGACA<br>(SEQ ID NO: 95) |
| PyqfDU-F | TTTGAAAGGAGGTTCTAACACTTTAATTTTTACGGGCCGGGCG<br>(SEQ ID NO: 96) |
| PyqfDU-R | TGTTAGAACCTCCTTTCAAATCATACATATGAG<br>(SEQ ID NO: 97) |
| PyqfDD-F | ACATAATTGGTAAGACCAATTGAGATGAAAGGGGGTTCTTTTTGTATGG<br>(SEQ ID NO: 98) |
| PyqfDD-R | ATTGGTCTTACCAATTATGTATGATTTGAAAGGAGGTTCTAACACTTT<br>(SEQ ID NO: 99) |
| PyqfD1-F | GATGAATTGGTAAGACCAATAAGGGGGTTCTTTTTGTATGGGTAAGG<br>(SEQ ID NO: 100) |
| PyqfD1-R | ATTGGTCTTACCAATTCATCTCATATGTATGATTTGAAAGGAGGTTCT<br>(SEQ ID NO: 101) |

Example 1: Construction of Strain 168-PR (1) Using the genome of *E. coli* K12 as a template, and P43-pdhR-F and P43-pdhR-R as primers, the pdhR fragment was obtained by amplification. Using the genome of *Bacillus subtilis* 168 as a template, and pdhR-FF and pdhR-FR as primers, the upstream homologous arm of pdhR was obtained by amplification; and using pdhR-RF and pdhR-RR as primers, the downstream homologous arm of pdhR was obtained by amplification. A lox71-spc-lox66-P43 cassette (having a sequence as shown in SEQ ID NO:12) containing the spectinomycin gene and the P43 promoter was artificially synthesized. The pdhR fragment, the upstream homologous arm of pdhR, the downstream homologous arm of pdhR and the lox71-spc-lox66-P43 cassette were fused by fusion PCR technology to obtain a fused gene fragment pdhRF-lox71-spc-lox66-P43-pdhR-pdhRR (referring to the instruction of Takara PrimerSTAR Max DNA Polymeraser for the experimental method).

(2) The fused fragment obtained in Step (1) was transformed into *Bacillus subtilis* 168 by electroporation at a voltage of 2.5 kV for 5 ms. After recovery at 37° C. for 5 h, the cells were inoculated into an LB plate coated with spectinomycin having a final concentration of 50 μg/mL, and incubated at 37° C. for 48 h. Single colonies on the plate were picked up. Using YZ_pdhR-F and YZ_pdhR-R as primers, colony PCR was performed, and a verification fragment with a size of 1700 bp was obtained by amplification (FIG. 1), indicating that the fused fragment was successfully integrated into the genome of *Bacillus subtilis* 168. The fragment was sequenced, and the strain corresponding to the fragment sequenced to be correct was the successfully constructed strain 168-PR.

Example 2: Construction of Pyruvate Biosensor

Figure 2:
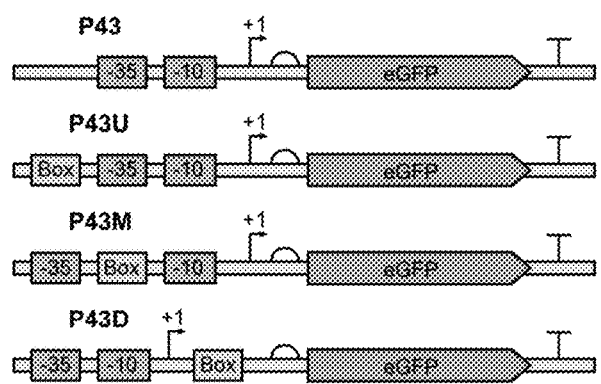
FIG. 2 shows the activity detection of pyruvate-responsive promoters having PdhR binding sites added at different sites.
Figure 2:
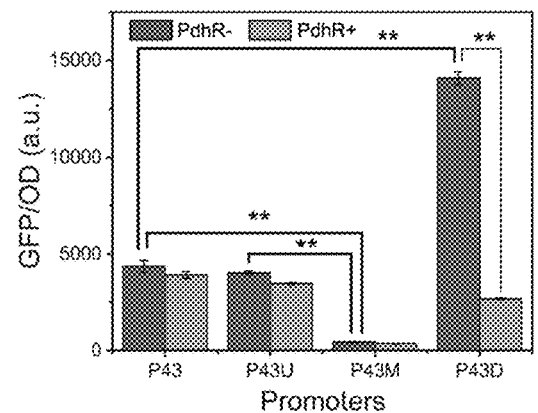

Using the laboratory-preserved plasmid PHT01-P43-GFP as a template (containing the P43 promoter and the reporter gene egfp positioned downstream of P43), and P43U-F/P43U-R, P43M-F/P43M-R and P43D-F/P43D-R as primers, a PdhR binding sequence was inserted into the −35 region, the −10 region or the +1 site of the P43 promoter in the plasmid by reverse PCR technology, to construct a hybrid promoter regulated by PdhR. In this way, the recombinant plasmids PHT01-P43U-GFP, PHT01-P43M-GFP and PHT01-P43D-GFP containing a pyruvate-responsive biosensor were obtained. Subsequently, the recombinant plasmids were respectively transformed into *Bacillus subtilis* 168 and the recombinant strain 168-PR obtained in Example 1 by electroporation, and then the fluorescence intensity of each recombinant plasmid in respective strain was detected according to the detection method 2. The results are shown in FIG. 2. The introduction of the pdhR binding sequence ATTGGTATGACCAAT (SEQ ID NO:2) into the P43 promoter affects the strength of the promoter itself. The activity of P43D is increased by 3.4 times relative to the P43 promoter, and the activity of P43U is reduced by 9.7 times relative to the P43 promoter. In addition, when pdhR is present in the strain, the activity of P43D is decreased by 4.2 times, indicating that pdhR can inhibit the activity of the promoter P43D.

Example 3: In Vitro Verification of the Binding Constant of P43D and pdhR (1) Using the laboratory-preserved plasmid pET-28a as a template, and Z_PET28F and Z_PET28R as primers, a linearized vector pET-28a was obtained by PCR amplification. Using the genome of E. coli K12 as a template, and 28apdhRF and 28apdhRR as primers, a pdhR fragment containing a homologous arm was obtained by PCR amplification. Then the pdhR fragment was fused with the linearized vector pET-28a (see the product instruction for specific steps) by using the Gibson Assembly® Master Mix available from NEB, to obtain the recombinant plasmid pET-28a-pdhR. The recombinant plasmid was sequenced, and the plasmid sequenced to be correct was stored at −20° C.

(2) The recombinant plasmid obtained in Step (1) was transformed into competent E. coli BL21 cells (see the Basic Molecular Biology Operation Manual for the operation method) to obtain the recombinant strain E. coli BL21-pdhR containing the plasmid pET-28a-pdhR. Then the recombinant strain was streaked into solid LB medium containing kanamycin (50 g/mL) and cultured at 37° C. for 12 h. Single colonies were picked into 200 ml of a liquid LB medium containing kanamycin (50 μg/mL), and cultured at 37° C. and 220 rpm to an OD600 of 0.6. Then IPTG was added to the culture medium at a final concentration of 0.2 mM to induce the expression of the protein PdhR, and incubated at 16° C. and 180 rpm for 12 h.

Figure 3:
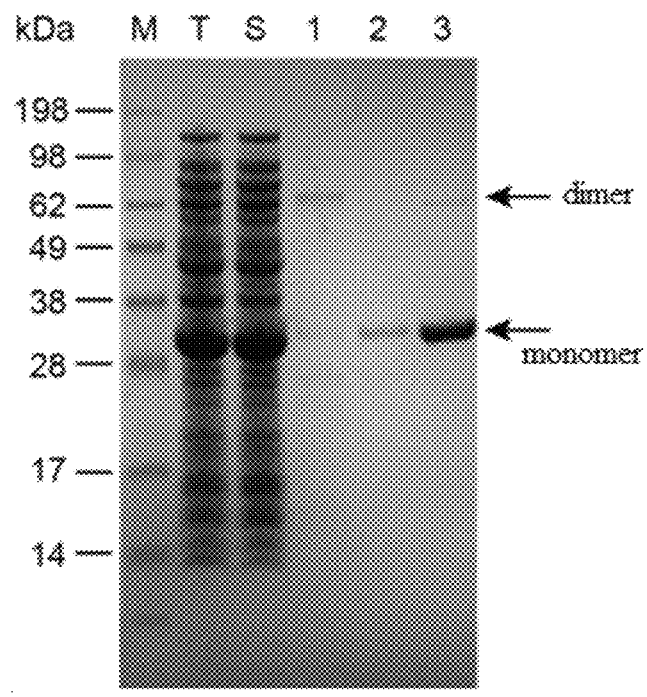
FIG. 3 is a SDS-PAGE electrophoretogram showing the purification of the transcription factor PdhR.
Figure 4:
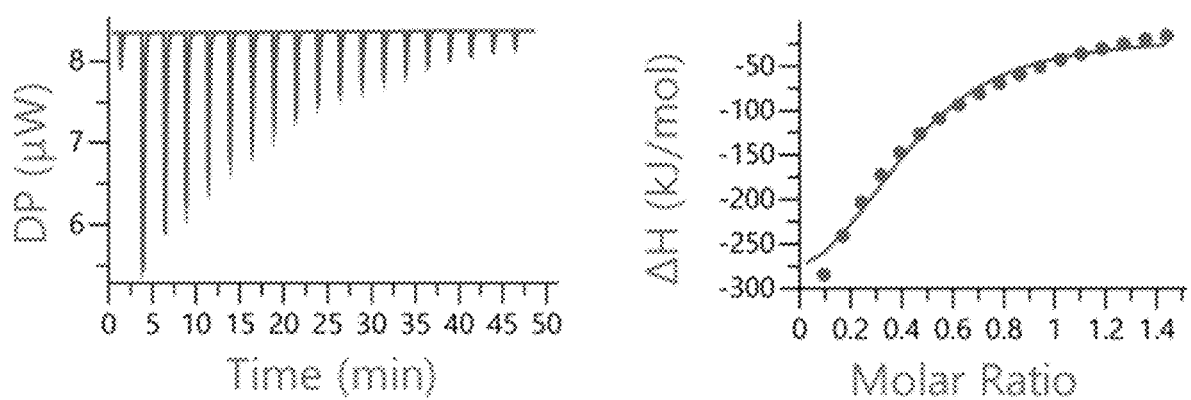
FIG. 4 is shows the ITC detection of the pyruvate-responsive promoter P43D with the transcription factor PdhR.

(3) The cell suspension obtained in Step (2) was centrifuged for 10 min at 4° C. and 4000 rpm. The cells were collected, and washed twice with 20 mM PBS buffer, and finally re-suspended in 20 mL of 20 mM PBS. Subsequently, the bacterial cells were homogenized by an ultrasonic homogenizer and centrifuged at 4° C. and 10,000 rpm for 30 min, and the supernatant was collected. Then the supernatant was loaded on a His GraviTrap column (GE Healthcare) and purified by AKTAFPLC (GE Healthcare). Then, the column was washed with 15 mL of buffer A (20 mM Tris, 0.5 M NaCl, 5 mM imidazole, pH=8.0) and 15 mL of buffer B (20 mM Tris, 0.5 M NaCl, 100 mM imidazole, PH=8.0). Finally, the protein PdhR was eluted off by using 5 mL of buffer C (20 mM Tris, 0.5 M NaCl, 200 mM imidazole, pH=8.0). Finally, the purity of pdhR was detected by SDS-PAGE (FIG. 3). The purified pdhR protein was then dialyzed against a dialysis solution (20 mM Tris, 0.5 M NaCl, 5% glycerol).

(4) Using the plasmid PHT01-P43D-GFP as a template, and P43DF and P43DR as primers, the DNA fragment P43D was obtained by PCR amplification. The DNA fragment was recovered using the GeneJET Gel Extraction Kit from Thermo Scientifi, and finally the P43D fragment was eluted off with the dialysis solution of Step (3).

(5) According to the detection method 3, the binding constant of the transcription factor pdhR with the DNA P43D was detected by isothermal thermometric titration. The result is shown in FIG. (4). The binding constant of P43D with pdhR is 1.4 μM, further indicating that pdhR can bind the constructed hybrid promoter P43D.

Figure 5:
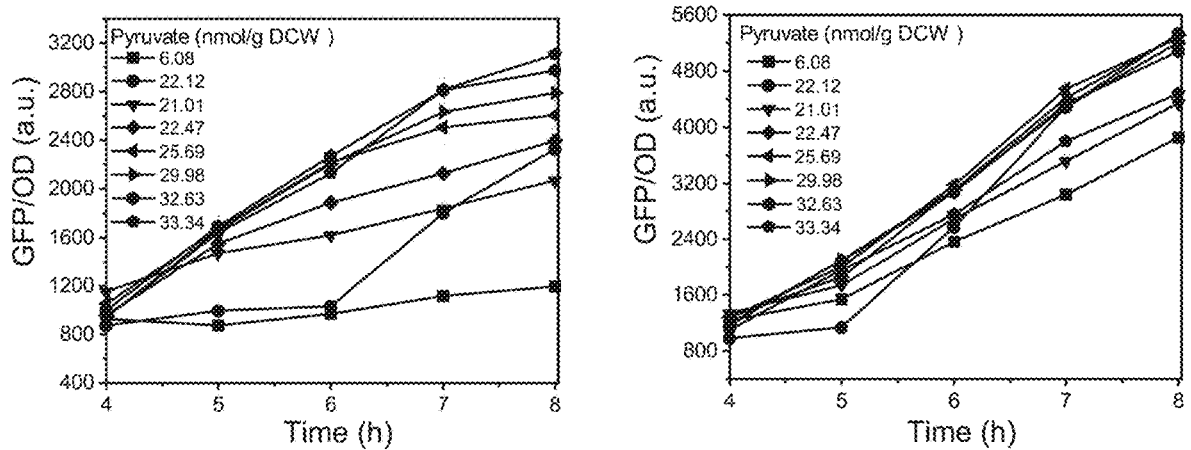
FIG. 5 is shows the change in fluorescence intensity of a pyruvate-responsive promoter with the concentration of pyruvate.

Example 4: Detection of Specificity and Response Range of Pyruvate Biosensor (1) According to the detection method 2, the relative fluorescence intensity of the strains 168 and 168-PR containing the plasmid PHT01-P43D-GFP in Experimental Example 2 was detected, and different concentrations of glucose and pyruvate were added to the medium to detect the response range to pyruvate of the constructed pyruvate biosensor, where the concentrations of glucose and pyruvate added in vitro were 0+0, 50+0, 50+5, 50+7.5, 50+10, 50+12.5, 50+15, and 50+20 g/L respectively. The experimental results are shown in FIG. 5. As the concentration of pyruvate increases, the relative fluorescence intensity of the pyruvate biosensor gradually increases, but the strain 168 (without FapR) is not affected by the concentration of pyruvate, indicating that the constructed pyruvate-responsive biosensor can respond to pyruvate. In order to further detect its response range to pyruvate, the intracellular pyruvate concentration in cells cultured under these conditions was detected by the detection method 1 and the data was fitted to the Hill equation $$\left(y = y_{min} + (y_{max} - y_{min})\frac{x^n}{K^n + x^n}\right).$$

Figure 6:
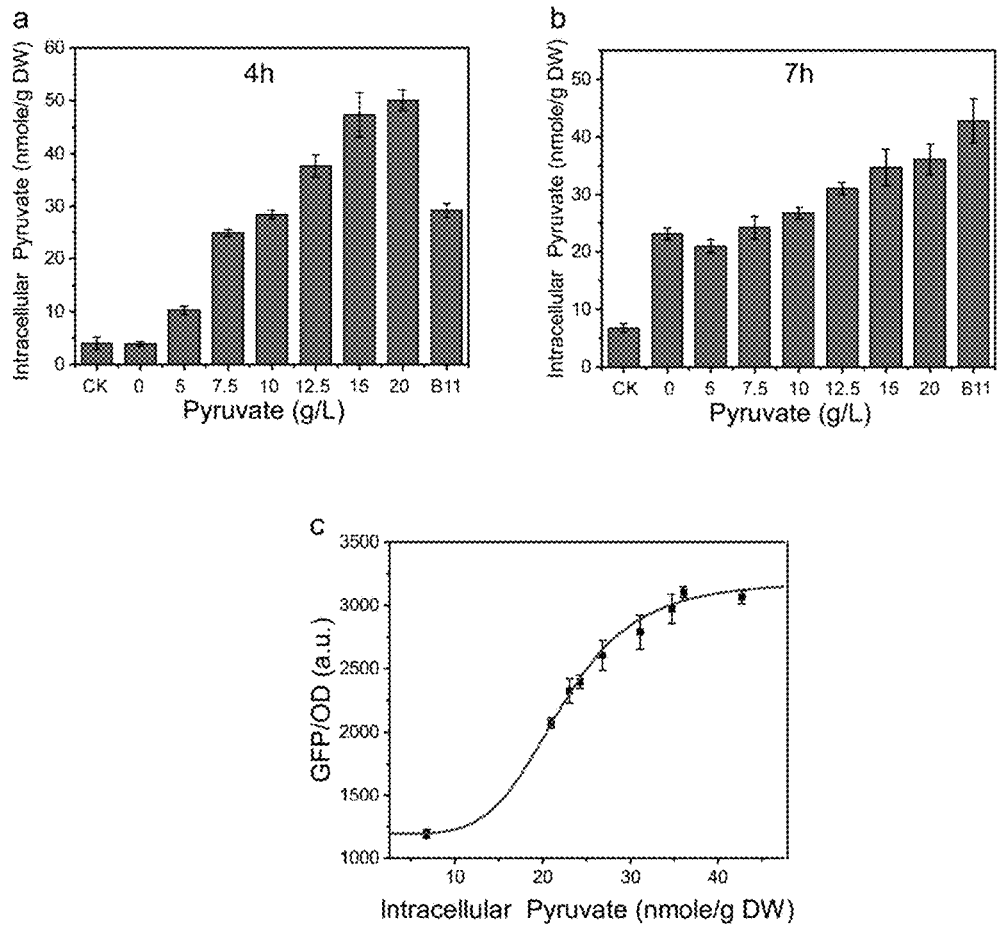
FIG. 6 shows the detection of the pyruvate response range of a pyruvate-responsive promoter.

The results show that the constructed pyruvate-responsive biosensor has a response range to pyruvate of 10-35 nmol/g DCW (FIG. 6).

Figure 7:
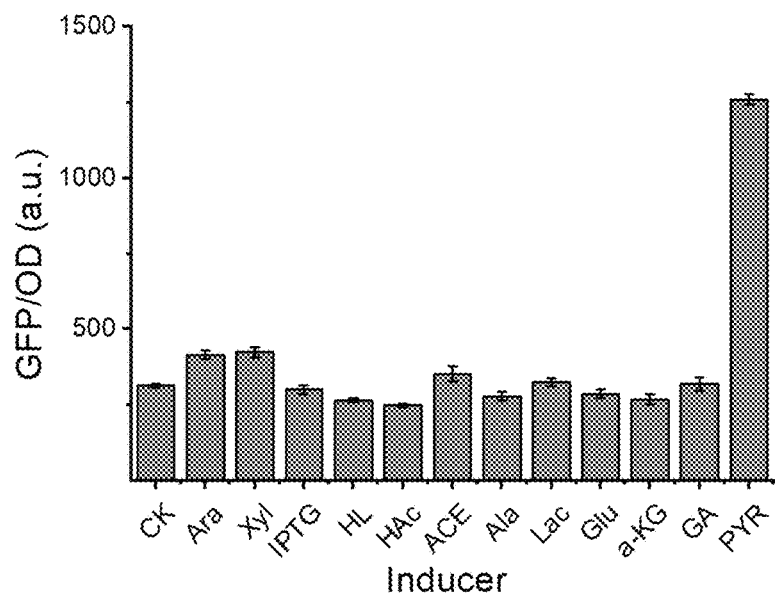
FIG. 7 is a diagram detecting the orthogonality of a pyruvate-responsive biosensor.

(2) To detect the specificity of the constructed pyruvate biosensor, the relative fluorescence intensity of the strain 168-PR containing the plasmid PHT01-P43D-GFP in the Experimental Example 2 was detected according to the detection method 2. Also, 5 g of an inducing agent was added to the medium, including inducing agents commonly used for Bacillus subtilis (arabinose, xylose and IPTG), pyruvate analogs (lactic acid, acetic acid, acetoin, alanine and lactose), other central metabolites (glucose, α-ketoglutaric acid and glucaric acid) and pyruvate. The results show that only pyruvate can significantly induce the activity of pyruvate biosensor, indicating that the constructed pyruvate biosensor has good specificity (FIG. 7).

Example 5: In Vitro Verification of the Binding Constant of Pyruvate with pdhR (1) The PdhR protein was obtained following Steps (1), (2) and (3) in Example 3.

(2) Sodium pyruvate was dissolved in a dialysis solution (20 mM Tris, 0.5 M NaCl, 5% glycerol) to give a final concentration of pyruvate of 500 μM.

Figure 8:
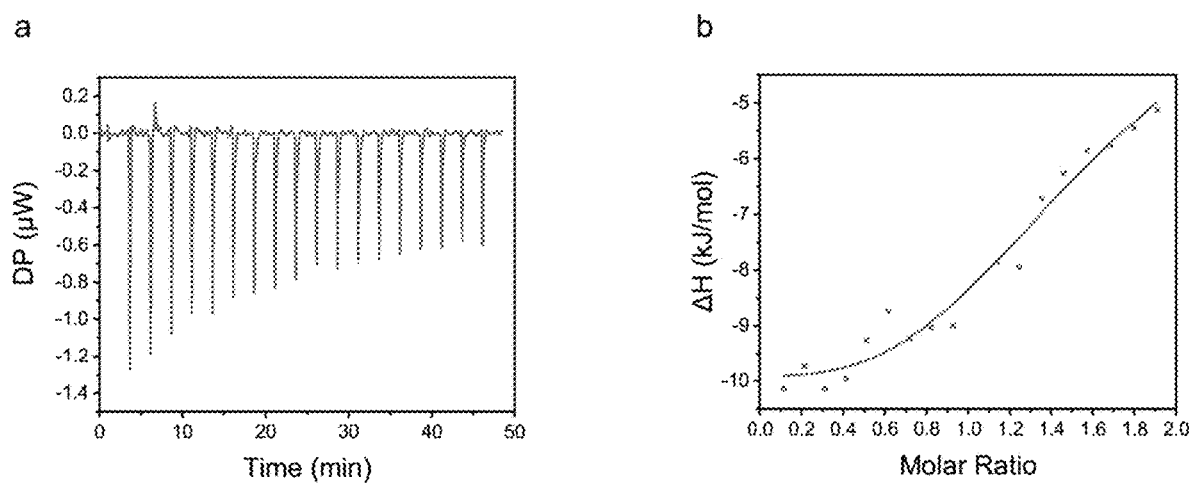
FIG. 8 shows the ITC detection of pyruvate with the transcription factor PdhR.

(3) According to the detection method 3, the binding constant of the transcription factor pdhR with pyruvate was detected by isothermal thermometric titration. The result is shown in FIG. 8. The binding constant of pyruvate with pdhR is 3.97 μM, further indicating that pdhR can respond to pyruvate.

Example 6: Optimization of pdhR Binding Site of Pyruvate Biosensor

Figure 9:
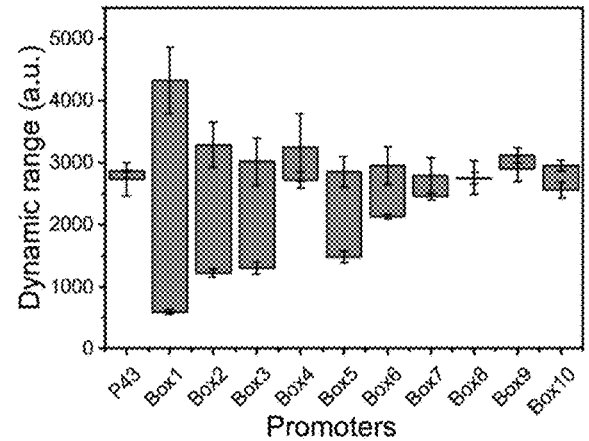
FIG. 9 shows the effect of changing the non-conserved region of the PdhR binding site on the dynamic range of a pyruvate biosensor, BOX1-BOX10 sequences therein being shown in SEQ ID NOs. 1-10, respectively.

Using the PHT01-P43D-GFP plasmid in Example 2 as a template, and pdhRBox-F1/R1, pdhRBox-F2/R2, pdhRBox- F3/R3, pdhRBox-F4/R4, pdhRBox-F5/R5, pdhRBox-F6/R6, pdhRBox-F7/R7, pdhRBox-F8/R8, pdhRBox-F9/R9, and pdhRBox-F10/R10 as primers respectively, the recombinant plasmids PHT01-P43BOX1-GFP, PHT01-P43BOX2-GFP, PHT01-P43BOX3-GFP, PHT01-P43BOX4-GFP, PHT01-P43BOX5-GFP, PHT01-P43BOX6-GFP, PHT01-P43BOX7-GFP, PHT01-P43BOX8-GFP, PHT01-P43BOX9-GFP and PHT01-P43BOX10-GFP were obtained by PCR amplification. The recombinant plasmids were sequenced, and the correctly sequenced plasmids were stored at −20° C. Subsequently, the recombinant plasmids were respectively transformed into *Bacillus subtilis* 168 and the recombinant strain 168-PR obtained in Example 1 by electroporation, and then the fluorescence intensity of each recombinant plasmid in respective strain was detected according to the detection method 2. The experimental results are shown in FIG. 9. The dynamic ranges of the recombinant plasmids PHT01-P43BOX1-GFP, PHT01-P43BOX2-GFP, PHT01-P43BOX3-GFP, PHT01-P43BOX4-GFP, PHT01-P43BOX5-GFP, PHT01-P43BOX6-GFP, PHT01-P43BOX7-GFP, PHT01-P43BOX8-GFP, PHT01-P43BOX9-GFP, and PHT01-P43BOX10-GFP are 7.2, 2.6, 2.3, 1.2, 1.9, 1.4, 1.1, 1.0, 1.0 and 1.1 times respectively. PHT01-P43BOX1-GFP has the largest dynamic range. In this example, the pdhR binding sequences include BOX1-BOX10 sequences in FIG. 9, which are respectively as shown in SEQ ID NOs. 1-10.

Figure 10:
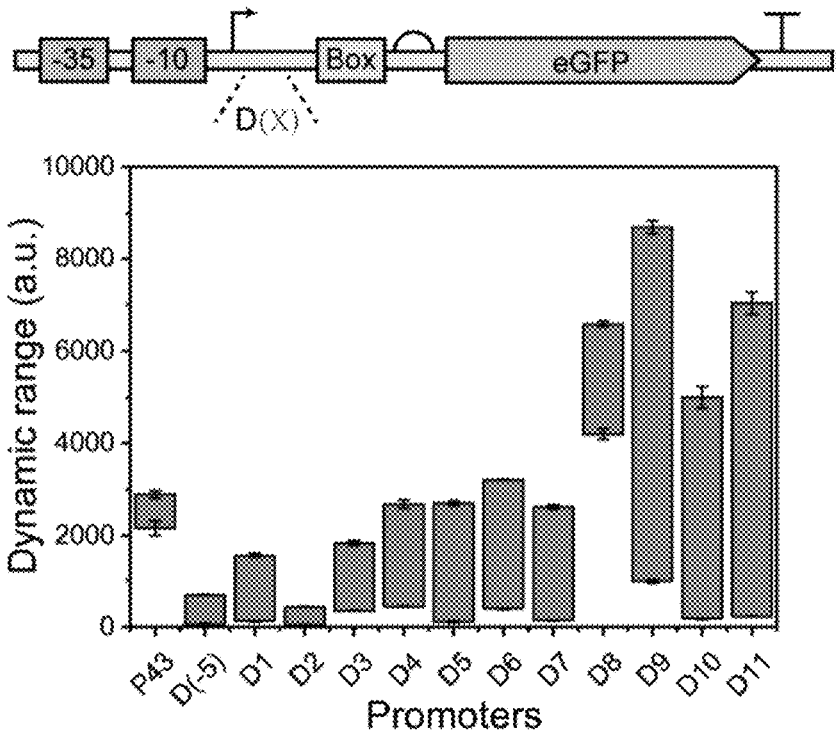
FIG. 10 shows the effect of changing the distance between the PdhR binding site and the +1 site on the dynamic range of a pyruvate biosensor.

Example 7: Optimization of the Distance Between the pdhR Binding Site and the +1 Site in the Promoter in the Pyruvate Biosensor Using the PHT01-P43BOX1-GFP plasmid in Example 6 as a template, and D(−5)F/R, D1F/R, D2F/R, D3F/R, D4F/R, D5F/R, D6F/R, D7F/R, D8F/R, D9F/R, D10F/R and D11F/R as primers respectively, the recombinant plasmids PHT01-P43D(−5)-GFP, PHT01-P43D1-GFP, PHT01-P43D2-GFP, PHT01-P43D3-GFP, PHT01-P43D4-GFP, PHT01-P43D5-GFP, PHT01-P43D6-GFP, PHT01-P43D7-GFP, PHT01-P43D8-GFP, PHT01-P43D9-GFP, PHT01-P43D10-GFP and PHT01-P43D11-GFP were obtained by PCR amplification, where D(−5) means a position that is upstream of the +1 site and 5 sites from the +1 site, D1 means a position that is downstream of the +1 site and 1 site from the +1 site, and so on. The recombinant plasmids were sequenced, and the correctly sequenced plasmid were stored at −20° C. Subsequently, the recombinant plasmids were respectively transformed into *Bacillus subtilis* 168 and the recombinant strain 168-PR obtained in Example 1 by electroporation, and then the fluorescence intensity of each recombinant plasmid in respective strain was detected according to the detection method 2. The experimental results are shown in FIG. 10. The dynamic ranges of the recombinant plasmids PHT01-P43D(−5)-GFP, PHT01-P43D1-GFP, PHT01-P43D2-GFP, PHT01-P43D3-GFP, PHT01-P43D4-GFP, PHT01-P43D5-GFP, PHT01-P43D6-GFP, PHT01-P43D7-GFP, PHT01-P43D8-GFP, PHT01-P43D9-GFP, PHT01-P43D10-GFP and PHT01-P43D11-GFP are 15.1, 12.9, 5.3, 6.1, 24.9, 8.3, 18.8, 1.6, 8.8, 28.1 and 31.7 times respectively.

Example 8: Construction of Phase-Dependent Pyruvate Biosensor (1) Using the laboratory-preserved plasmid PHT01-P43-GFP as a template, and Z_PHT01-F and Z_PHT01-R as primers, the linearized vector PHT01-GFP (with the P43 promoter being removed) was obtained by PCR amplification. Using the genome of *B. subtilis* 168 as a template, and PyteJ-F/R, Pywjc-F/R and PyqfD-F/R as primers respectively, $P_{yteJ}$, $P_{ywjc}$ and $P_{yqfD}$ fragments containing a homologous arm were obtained by PCR amplification. Then, the $P_{yteJ}$, $P_{ywjc}$ and $P_{yqfD}$ fragments were respectively fused with the linearized vector PHT01-GFP by using the Gibson Assembly® Master Mix from NEB (see the product instruction for specific steps) to obtain the recombinant plasmids PHT01-$P_{yteJ}$-GFP, PHT01-$P_{ywjc}$-GFP and PHT01-$P_{yqfD}$-GFP. The recombinant plasmid was sequenced, and the plasmid sequenced to be correct was stored at −20° C.

(2) Using the recombinant plasmid PHT01-$P_{yteJ}$-GFP obtained in Step (1) as a template, and PyteJU-F/PyteJU-R, PyteJD-F/PyteJD-R, and PyteJ1-F/PyteJ1-R as primers respectively, a PdhR binding sequence was inserted into the −35 region, the −10 region or the +1 site of the P43 promoter in the plasmid by reverse PCR technology, to construct a hybrid promoter regulated by PdhR. In this way, the recombinant plasmids PHT01-PyteJU-GFP, PHT01-PyteJD-GFP, and PHT01-PyteJ1-GFP containing a pyruvate-responsive biosensor were obtained.

(3) Using the recombinant plasmid PHT01-$P_{ywjc}$-GFP obtained in Step (1) as a template, and PywjcU-F/PywjcU-R, PywjcD-F/PywjcD-R and Pywjc1-F/Pywjc1-R as primers respectively, a PdhR binding sequence was inserted into the −35 region, the −10 region or the +1 site of the P43 promoter in the plasmid by reverse PCR technology, to construct a hybrid promoter regulated by PdhR. In this way, the recombinant plasmids PHT01-PywjcU-GFP, PHT01-PywjcD-GFP and PHT01-Pywjc1-GFP containing a pyruvate-responsive biosensor were obtained.

(4) Using the recombinant plasmid PHT01-PyqfD-GFP obtained in Step (1) as a template, and PyqfDU-F/PywjcU-R, PyqfDD-F/PyqfDD-R and PyqfD1-F/PyqfD1-R as primers respectively, a PdhR binding sequence was inserted into the −35 region, the −10 region or the +1 site of the P43 promoter in the plasmid by reverse PCR technology, to construct a hybrid promoter regulated by PdhR. In this way, the recombinant plasmids PHT01-PyqfDU-GFP, PHT01-PyqfDD-GFP and PHT01-PyqfD1-GFP containing a pyruvate-responsive biosensor were obtained.

Figure 11:
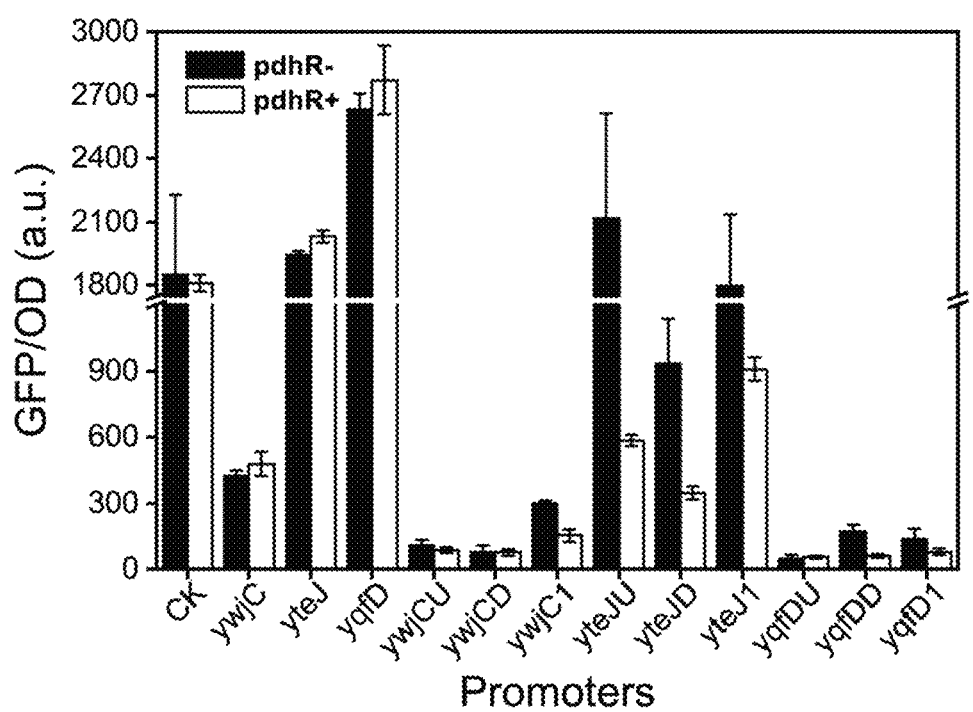
FIG. 11 shows the fluorescence intensity of a phase-dependent pyruvate biosensor.

(5) The recombinant plasmids PHT01-$P_{yteJ}$-GFP, PHT01-$P_{ywjc}$-GFP, PHT01-$P_{yqfD}$-GFP, PHT01-PyteJU-GFP, PHT01-PyteJD-GFP, PHT01-PyteJ1-GFP, PHT01-PywjcU-GFP, PHT01-PywjcD-GFP, PHT01-Pywjc1-GFP, PHT01-PyqfDU-GFP, PHT01-PyqfDD-GFP and PHT01-PyqfD1-GFP were respectively transformed into *Bacillus subtilis* 168 and the recombinant strain 168-PR obtained in Example 1 by electroporation. Then the fluorescence intensity of each recombinant plasmid in respective strains was detected according to the detection method 2. The results are shown in FIG. 11. The dynamic ranges of the biosensors PHT01-PywjcU-GFP, PHT01-PywjcD-GFP, PHT01-Pywjc1-GFP, PHT01-PyteJU-GFP, PHT01-PyteJD-GFP, PHT01-PyteJ1-GFP, PHT01-PyqfDU-GFP, PHT01-PyqfDD-GFP and PHT01-PyqfD1-GFP are 1.3, 1.2, 1.9, 3.6, 2.7, 2.0, 1.0, 2.9 and 1.8 times, respectively.

The above-described embodiments are merely preferred embodiments for the purpose of fully illustrating the present invention, and the scope of the present invention is not limited thereto. Equivalent substitutions or modifications can be made by those skilled in the art based on the present invention, which are within the scope of the present invention as defined by the claims.

What is claimed is:

1. A pyruvate-responsive biosensor, comprising a PdhR gene, a P43 promoter, and a PdhR (pyruvate dehydrogenase complex regulator) binding sequence inserted in the P43 promoter,
wherein the nucleotide sequence of the PdhR binding sequence is as shown in SEQ ID NO:1, SEQ ID NO:2, SEQ ID NO:3 or SEQ ID NO:5.

2. The pyruvate-responsive biosensor according to claim 1, wherein an insertion site of the PdhR binding sequence in the P43 promoter is the +1 site, the 5th site upstream of the +1 site or one of the 1st to 11th sites downstream of the +1 site.

3. The pyruvate-responsive biosensor according to claim 1, wherein the PdhR gene is integrated upstream of the ycgB gene in a *Bacillus subtilis* genome.

4. The pyruvate-responsive biosensor according to claim 1, wherein the nucleotide sequence of the PdhR gene is as shown in SEQ ID NO:11.

5. The pyruvate-responsive biosensor according to claim 1, wherein the pyruvate-responsive biosensor further comprises a reporter gene egfp located downstream of the P43 promoter.

6. The pyruvate-responsive biosensor according to claim 5, wherein the P43 promoter, the PdhR binding sequence and the reporter gene egfp are located in the vector PHT01.

* * * * *

SEQUENCE LISTING

<160> NUMBER OF SEQ ID NOS: 101

<210> SEQ ID NO 1
<211> LENGTH: 15
<212> TYPE: DNA
<213> ORGANISM: Artificial sequence
<220> FEATURE:
<223> OTHER INFORMATION: PdhR binding sequence

<400> SEQUENCE: 1
attggtaaga ccaat                                                    15

<210> SEQ ID NO 2
<211> LENGTH: 15
<212> TYPE: DNA
<213> ORGANISM: Artificial sequence
<220> FEATURE:
<223> OTHER INFORMATION: PdhR binding sequence

<400> SEQUENCE: 2
attggtatga ccaat                                                    15

<210> SEQ ID NO 3
<211> LENGTH: 15
<212> TYPE: DNA
<213> ORGANISM: Artificial sequence
<220> FEATURE:
<223> OTHER INFORMATION: PdhR binding sequence

<400> SEQUENCE: 3
attggtaata ccaat                                                    15

<210> SEQ ID NO 4
<211> LENGTH: 15
<212> TYPE: DNA
<213> ORGANISM: Artificial sequence
<220> FEATURE:
<223> OTHER INFORMATION: PdhR binding sequence

<400> SEQUENCE: 4
attggttaaa ccaat                                                    15

<210> SEQ ID NO 5
<211> LENGTH: 15
<212> TYPE: DNA
<213> ORGANISM: Artificial sequence
<220> FEATURE:
<223> OTHER INFORMATION: PdhR binding sequence

<400> SEQUENCE: 5
attggtatta ccaat                                                    15

<210> SEQ ID NO 6
<211> LENGTH: 15
<212> TYPE: DNA
<213> ORGANISM: Artificial sequence
<220> FEATURE:
<223> OTHER INFORMATION: PdhR binding sequence

<400> SEQUENCE: 6
attggtttaa ccaat                                                    15

<210> SEQ ID NO 7
<211> LENGTH: 15
<212> TYPE: DNA
<213> ORGANISM: Artificial sequence

```
<220> FEATURE:
<223> OTHER INFORMATION: PdhR binding sequence

<400> SEQUENCE: 7
attggtacta ccaat                                                      15

<210> SEQ ID NO 8
<211> LENGTH: 15
<212> TYPE: DNA
<213> ORGANISM: Artificial sequence
<220> FEATURE:
<223> OTHER INFORMATION: PdhR binding sequence

<400> SEQUENCE: 8
attggtagta ccaat                                                      15

<210> SEQ ID NO 9
<211> LENGTH: 15
<212> TYPE: DNA
<213> ORGANISM: Artificial sequence
<220> FEATURE:
<223> OTHER INFORMATION: PdhR binding sequence

<400> SEQUENCE: 9
attggttgaa ccaat                                                      15

<210> SEQ ID NO 10
<211> LENGTH: 15
<212> TYPE: DNA
<213> ORGANISM: Artificial sequence
<220> FEATURE:
<223> OTHER INFORMATION: PdhR binding sequence

<400> SEQUENCE: 10
attggtgaca ccaat                                                      15

<210> SEQ ID NO 11
<211> LENGTH: 765
<212> TYPE: DNA
<213> ORGANISM: Artificial sequence
<220> FEATURE:
<223> OTHER INFORMATION: PdhR gene

<400> SEQUENCE: 11
atggcctaca gcaaaatccg ccaaccaaaa ctctccgatg tgattgagca gcaactggag       60 ttttttgatcc tcgaaggcac tctccgcccg ggcgaaaaac tcccaccgga acgcgaactg     120
gcaaaacagt tgacgtctc ccgtccctcc ttgcgtgagg cgattcaacg tctcgaagcg      180
aagggcttgt tgcttcgtcg ccagggtggc ggcacttttg tccagagcag cctatggcaa     240
agcttcagcg atccgctggt ggagctgctc tccgaccatc ctgagtcaca gtatgacttg     300
ctcgaaacac gacacgccct ggaaggtatc gccgcttatt acgccgcgct gcgtagtacc     360
gatgaagaca aggaacgcat ccgtgaactc caccacgcca tagagctggc gcagcagtct     420
ggcgatctgg acgcggaatc aaacgccgta ctccagtatc agattgccgt caccgaagcg     480
gcccacaatg tggttctgct tcatctgcta aggtgtatgg agccgatgtt ggcccagaat     540
gtccgccaga acttcgaatt gctctattcg cgtcgcgaga tgctgccgct ggtgagtagt     600
caccgcaccc gcatatttga agcgattatg gccggtaagc cggaagaagc gcgcgaagca     660
tcgcatcgcc atctgccctt tatcgaagaa attttgctcg acagaagtcg tgaagagagc     720
cgccgtgagc gttctctgcg tcgtctggag caacgaaaga attag                     765
```

<210> SEQ ID NO 12
<211> LENGTH: 1106
<212> TYPE: DNA
<213> ORGANISM: Artificial sequence
<220> FEATURE:
<223> OTHER INFORMATION: lox71-spc-lox66-P43 cassette

<400> SEQUENCE: 12

| | | | | | |
|---|---|---|---|---|---|
| gtaccgttcg | tatagcatac | attatacgaa | gttatcgatt | ttcgttcgtg | aatacatgtt | 60 |
| ataataacta | taactaataa | cgtaacgtga | ctggcaagag | atattttaa | aacaatgaat | 120 |
| aggtttacac | ttactttagt | tttatggaaa | tgaaagatca | tatcatatat | aatctagaat | 180 |
| aaaattaact | aaaataatta | ttatctagat | aaaaaattta | gaagccaatg | aaatctataa | 240 |
| ataaactaaa | ttaagtttat | ttaattaaca | actatggata | taaaataggt | actaatcaaa | 300 |
| atagtgagga | ggatatattt | gaatacatac | gaacaagtta | ataaagtgaa | aaaaatactt | 360 |
| cggaaacatt | taaaaaataa | ccttattggt | acttacatgt | ttggatcagg | agttgagagt | 420 |
| ggactaaaac | caaatagtga | tcttgacttt | ttagtcgtcg | tatctgaacc | attgacagat | 480 |
| caaagtaaag | aaatacttat | acaaaaaatt | agacctattt | caaaaaaaat | aggagataaa | 540 |
| agcaacttac | gatatattga | attaacaatt | attattcagc | aagaaatggt | accgtggaat | 600 |
| catcctccca | aacaagaatt | tatttatgga | gaatggttac | aagagcttta | tgaacaagga | 660 |
| tacattcctc | agaaggaatt | aaattcagat | ttaaccataa | tgcttaccaa | agcaaaacga | 720 |
| aaaaataaaa | gaatatacgg | aaattatgac | ttagaggaat | tactacctga | tattccattt | 780 |
| tctgatgtga | gaagagccat | tatggattcg | tcagaggaat | aatagataa | ttatcaggat | 840 |
| gatgaaacca | actctatatt | aactttatgc | cgtatgattt | taactatgga | cacgggtaaa | 900 |
| atcataccaa | aagatattgc | gggaaatgca | gtggctgaat | cttctccatt | agaacatagg | 960 |
| gagagaattt | tgttagcagt | tcgtagttat | cttggagaga | atattgaatg | gactaatgaa | 1020 |
| aatgtaaatt | taactataaa | ctatttaaat | aacagattaa | aaaaattata | aataacttcg | 1080 |
| tatagcatac | attatacgaa | cggtag | | | | 1106 |

<210> SEQ ID NO 13
<211> LENGTH: 200
<212> TYPE: DNA
<213> ORGANISM: Artificial sequence
<220> FEATURE:
<223> OTHER INFORMATION: P43 promoter

<400> SEQUENCE: 13

| | | | | | |
|---|---|---|---|---|---|
| ccaaggacgc | tgccgccggg | gctgtttgcg | tttttgccgt | gatttcgtgt | atcattggtt | 060 |
| tacttatttt | tttgccaaag | ctgtaatggc | tgaaaattct | tacatttatt | ttacattttt | 120 |
| agaaatgggc | gtgaaaaaaa | gcgcgcgatt | atgtaaaata | taaagtgata | gcggtaccct | 180 |
| cgagaaaagg | aggaaaaaaa | | | | | 200 |

<210> SEQ ID NO 14
<211> LENGTH: 52
<212> TYPE: DNA
<213> ORGANISM: Artificial sequence
<220> FEATURE:
<223> OTHER INFORMATION: Primer

<400> SEQUENCE: 14
cggtaccatt ggtatgacca atctcgagaa aaggaggaaa aaaatgggt aa            52

```
<210> SEQ ID NO 15
<211> LENGTH: 55
<212> TYPE: DNA
<213> ORGANISM: Artificial sequence
<220> FEATURE:
<223> OTHER INFORMATION: Primer

<400> SEQUENCE: 15
tctcgagatt ggtcatacca atggtaccgc tatcacttta tattttacat aatcg          55

<210> SEQ ID NO 16
<211> LENGTH: 46
<212> TYPE: DNA
<213> ORGANISM: Artificial sequence
<220> FEATURE:
<223> OTHER INFORMATION: Primer

<400> SEQUENCE: 16
attggtatga ccaatctgta atggctgaaa attcttacat ttattt                    46

<210> SEQ ID NO 17
<211> LENGTH: 48
<212> TYPE: DNA
<213> ORGANISM: Artificial sequence
<220> FEATURE:
<223> OTHER INFORMATION: Primer

<400> SEQUENCE: 17
tacagattgg tcataccaat ctttggcaaa aaataagta aaccaatg                   48

<210> SEQ ID NO 18
<211> LENGTH: 48
<212> TYPE: DNA
<213> ORGANISM: Artificial sequence
<220> FEATURE:
<223> OTHER INFORMATION: Primer

<400> SEQUENCE: 18
aaaaaattgg tatgaccaat gcgcgcgatt atgtaaaata taaagtga                  48

<210> SEQ ID NO 19
<211> LENGTH: 43
<212> TYPE: DNA
<213> ORGANISM: Artificial sequence
<220> FEATURE:
<223> OTHER INFORMATION: Primer

<400> SEQUENCE: 19
attggtcata ccaatttttt ttcacgccca tttctaaaaa tgt                       43

<210> SEQ ID NO 20
<211> LENGTH: 46
<212> TYPE: DNA
<213> ORGANISM: Artificial sequence
<220> FEATURE:
<223> OTHER INFORMATION: Primer

<400> SEQUENCE: 20
ggtaagagag gaatgtacac atggcctaca gcaaaatccg ccaacc                    46

<210> SEQ ID NO 21
<211> LENGTH: 45
<212> TYPE: DNA
<213> ORGANISM: Artificial sequence
<220> FEATURE:
<223> OTHER INFORMATION: Primer
```

<400> SEQUENCE: 21
cccgtctagc cttgcccta attctttcgt tgctccagac gacgc          45

<210> SEQ ID NO 22
<211> LENGTH: 29
<212> TYPE: DNA
<213> ORGANISM: Artificial sequence
<220> FEATURE:
<223> OTHER INFORMATION: Primer

<400> SEQUENCE: 22
gatttggttc ttgatcgggc ttgtcttta          29

<210> SEQ ID NO 23
<211> LENGTH: 51
<212> TYPE: DNA
<213> ORGANISM: Artificial sequence
<220> FEATURE:
<223> OTHER INFORMATION: Primer

<400> SEQUENCE: 23
gtgtgaaatt gttatccgct cttacttcat tcttccgctt cctcctttca a          51

<210> SEQ ID NO 24
<211> LENGTH: 47
<212> TYPE: DNA
<213> ORGANISM: Artificial sequence
<220> FEATURE:
<223> OTHER INFORMATION: Primer

<400> SEQUENCE: 24
gtctggagca acgaaagaat tagggcaag gctagacggg acttacc          47

<210> SEQ ID NO 25
<211> LENGTH: 24
<212> TYPE: DNA
<213> ORGANISM: Artificial sequence
<220> FEATURE:
<223> OTHER INFORMATION: Primer

<400> SEQUENCE: 25
aacgagttca ctgaccggca cacc          24

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
gctagccata tggctgccgc          20

<210> SEQ ID NO 27
<211> LENGTH: 23
<212> TYPE: DNA
<213> ORGANISM: Artificial sequence
<220> FEATURE:
<223> OTHER INFORMATION: Primer

<400> SEQUENCE: 27
atgactggtg gacagcaaat ggg          23

<210> SEQ ID NO 28
<211> LENGTH: 48

```
<212> TYPE: DNA
<213> ORGANISM: Artificial sequence
<220> FEATURE:
<223> OTHER INFORMATION: Primer

<400> SEQUENCE: 28
atttgctgtc caccagtcat ctaattcttt cgttgctcca gacgacgc          48

<210> SEQ ID NO 29
<211> LENGTH: 46
<212> TYPE: DNA
<213> ORGANISM: Artificial sequence
<220> FEATURE:
<223> OTHER INFORMATION: Primer

<400> SEQUENCE: 29
gcggcagcca tatggctagc atggcctaca gcaaaatccg ccaacc            46

<210> SEQ ID NO 30
<211> LENGTH: 22
<212> TYPE: DNA
<213> ORGANISM: Artificial sequence
<220> FEATURE:
<223> OTHER INFORMATION: Primer

<400> SEQUENCE: 30
acagccattg aacatacggt tg                                      22

<210> SEQ ID NO 31
<211> LENGTH: 28
<212> TYPE: DNA
<213> ORGANISM: Artificial sequence
<220> FEATURE:
<223> OTHER INFORMATION: Primer

<400> SEQUENCE: 31
tttttttcct ccttttctcg agattggt                                28

<210> SEQ ID NO 32
<211> LENGTH: 24
<212> TYPE: DNA
<213> ORGANISM: Artificial sequence
<220> FEATURE:
<223> OTHER INFORMATION: Primer

<400> SEQUENCE: 32
ccgcattggt aagaccaatg tacg                                    24

<210> SEQ ID NO 33
<211> LENGTH: 24
<212> TYPE: DNA
<213> ORGANISM: Artificial sequence
<220> FEATURE:
<223> OTHER INFORMATION: Primer

<400> SEQUENCE: 33
tacattggtt taaccaatgc ggcc                                    24

<210> SEQ ID NO 34
<211> LENGTH: 24
<212> TYPE: DNA
<213> ORGANISM: Artificial sequence
<220> FEATURE:
<223> OTHER INFORMATION: Primer

<400> SEQUENCE: 34
```
ccgcattggt atgaccaatg tacg                                              24

<210> SEQ ID NO 35
<211> LENGTH: 24
<212> TYPE: DNA
<213> ORGANISM: Artificial sequence
<220> FEATURE:
<223> OTHER INFORMATION: Primer

<400> SEQUENCE: 35
tacattggtc ataccaatgc ggcc                                              24

<210> SEQ ID NO 36
<211> LENGTH: 24
<212> TYPE: DNA
<213> ORGANISM: Artificial sequence
<220> FEATURE:
<223> OTHER INFORMATION: Primer

<400> SEQUENCE: 36
ccgcattggt aataccaatg tacg                                              24

<210> SEQ ID NO 37
<211> LENGTH: 24
<212> TYPE: DNA
<213> ORGANISM: Artificial sequence
<220> FEATURE:
<223> OTHER INFORMATION: Primer

<400> SEQUENCE: 37
tacattggta ttaccaatgc ggcc                                              24

<210> SEQ ID NO 38
<211> LENGTH: 24
<212> TYPE: DNA
<213> ORGANISM: Artificial sequence
<220> FEATURE:
<223> OTHER INFORMATION: Primer

<400> SEQUENCE: 38
ccgcattggt taaaccaatg tacg                                              24

<210> SEQ ID NO 39
<211> LENGTH: 24
<212> TYPE: DNA
<213> ORGANISM: Artificial sequence
<220> FEATURE:
<223> OTHER INFORMATION: Primer

<400> SEQUENCE: 39
tacattggtt taaccaatgc ggcc                                              24

<210> SEQ ID NO 40
<211> LENGTH: 24
<212> TYPE: DNA
<213> ORGANISM: Artificial sequence
<220> FEATURE:
<223> OTHER INFORMATION: Primer

<400> SEQUENCE: 40
ccgcattggt attaccaatg tacg                                              24

<210> SEQ ID NO 41
<211> LENGTH: 24
<212> TYPE: DNA
<213> ORGANISM: Artificial sequence

```
<220> FEATURE:
<223> OTHER INFORMATION: Primer

<400> SEQUENCE: 41
tacattggta ataccaatgc ggcc                                              24

<210> SEQ ID NO 42
<211> LENGTH: 24
<212> TYPE: DNA
<213> ORGANISM: Artificial sequence
<220> FEATURE:
<223> OTHER INFORMATION: Primer

<400> SEQUENCE: 42
ccgcattggt ttaaccaatg tacg                                              24

<210> SEQ ID NO 43
<211> LENGTH: 24
<212> TYPE: DNA
<213> ORGANISM: Artificial sequence
<220> FEATURE:
<223> OTHER INFORMATION: Primer

<400> SEQUENCE: 43
tacattggtt aaaccaatgc ggcc                                              24

<210> SEQ ID NO 44
<211> LENGTH: 24
<212> TYPE: DNA
<213> ORGANISM: Artificial sequence
<220> FEATURE:
<223> OTHER INFORMATION: Primer

<400> SEQUENCE: 44
ccgcattggt actaccaatg tacg                                              24

<210> SEQ ID NO 45
<211> LENGTH: 24
<212> TYPE: DNA
<213> ORGANISM: Artificial sequence
<220> FEATURE:
<223> OTHER INFORMATION: Primer

<400> SEQUENCE: 45
tacattggta gtaccaatgc ggcc                                              24

<210> SEQ ID NO 46
<211> LENGTH: 24
<212> TYPE: DNA
<213> ORGANISM: Artificial sequence
<220> FEATURE:
<223> OTHER INFORMATION: Primer

<400> SEQUENCE: 46
ccgcattggt agtaccaatg tacg                                              24

<210> SEQ ID NO 47
<211> LENGTH: 24
<212> TYPE: DNA
<213> ORGANISM: Artificial sequence
<220> FEATURE:
<223> OTHER INFORMATION: Primer

<400> SEQUENCE: 47
tacattggta ctaccaatgc ggcc                                              24
```

```
<210> SEQ ID NO 48
<211> LENGTH: 24
<212> TYPE: DNA
<213> ORGANISM: Artificial sequence
<220> FEATURE:
<223> OTHER INFORMATION: Primer

<400> SEQUENCE: 48
ccgcattggt tgaaccaatg tacg                                      24

<210> SEQ ID NO 49
<211> LENGTH: 24
<212> TYPE: DNA
<213> ORGANISM: Artificial sequence
<220> FEATURE:
<223> OTHER INFORMATION: Primer

<400> SEQUENCE: 49
tacattggtt caaccaatgc ggcc                                      24

<210> SEQ ID NO 50
<211> LENGTH: 23
<212> TYPE: DNA
<213> ORGANISM: Artificial sequence
<220> FEATURE:
<223> OTHER INFORMATION: Primer

<400> SEQUENCE: 50
ccgcattggt gacaccaatg tac                                       23

<210> SEQ ID NO 51
<211> LENGTH: 24
<212> TYPE: DNA
<213> ORGANISM: Artificial sequence
<220> FEATURE:
<223> OTHER INFORMATION: Primer

<400> SEQUENCE: 51
tacattggtg tcaccaatgc ggcc                                      24

<210> SEQ ID NO 52
<211> LENGTH: 46
<212> TYPE: DNA
<213> ORGANISM: Artificial sequence
<220> FEATURE:
<223> OTHER INFORMATION: Primer

<400> SEQUENCE: 52
gtaaaattgg taagaccaat ataaagtgat agcggtaccc tcgaga              46

<210> SEQ ID NO 53
<211> LENGTH: 40
<212> TYPE: DNA
<213> ORGANISM: Artificial sequence
<220> FEATURE:
<223> OTHER INFORMATION: Primer

<400> SEQUENCE: 53
attggtctta ccaattttac ataatcgcgc gcttttttc                      40

<210> SEQ ID NO 54
<211> LENGTH: 45
<212> TYPE: DNA
<213> ORGANISM: Artificial sequence
<220> FEATURE:
<223> OTHER INFORMATION: Primer
```

<400> SEQUENCE: 54
ataaaattgg taagaccaat gtgatagcgg taccctcgag aaaag					45

<210> SEQ ID NO 55
<211> LENGTH: 53
<212> TYPE: DNA
<213> ORGANISM: Artificial sequence
<220> FEATURE:
<223> OTHER INFORMATION: Primer

<400> SEQUENCE: 55
ctatcacatt ggtcttacca attttatatt ttacataatc gcgcgctttt ttt				53

<210> SEQ ID NO 56
<211> LENGTH: 43
<212> TYPE: DNA
<213> ORGANISM: Artificial sequence
<220> FEATURE:
<223> OTHER INFORMATION: Primer

<400> SEQUENCE: 56
attggtctta ccaatcttta tattttacat aatcgcgcgc ttt						43

<210> SEQ ID NO 57
<211> LENGTH: 44
<212> TYPE: DNA
<213> ORGANISM: Artificial sequence
<220> FEATURE:
<223> OTHER INFORMATION: Primer

<400> SEQUENCE: 57
taaagattgg taagaccaat tgatagcggt accctcgaga aaag						44

<210> SEQ ID NO 58
<211> LENGTH: 44
<212> TYPE: DNA
<213> ORGANISM: Artificial sequence
<220> FEATURE:
<223> OTHER INFORMATION: Primer

<400> SEQUENCE: 58
cattggtctt accaatactt tatattttac ataatcgcgc gctt					44

<210> SEQ ID NO 59
<211> LENGTH: 43
<212> TYPE: DNA
<213> ORGANISM: Artificial sequence
<220> FEATURE:
<223> OTHER INFORMATION: Primer

<400> SEQUENCE: 59
aagtattggt aagaccaatg atagcggtac cctcgagaaa agg						43

<210> SEQ ID NO 60
<211> LENGTH: 43
<212> TYPE: DNA
<213> ORGANISM: Artificial sequence
<220> FEATURE:
<223> OTHER INFORMATION: Primer

<400> SEQUENCE: 60
aagtgattgg taagaccaat atagcggtac cctcgagaaa agg						43

<210> SEQ ID NO 61

```
<211> LENGTH: 43
<212> TYPE: DNA
<213> ORGANISM: Artificial sequence
<220> FEATURE:
<223> OTHER INFORMATION: Primer

<400> SEQUENCE: 61
attggtctta ccaatcactt tatattttac ataatcgcgc gct                    43

<210> SEQ ID NO 62
<211> LENGTH: 44
<212> TYPE: DNA
<213> ORGANISM: Artificial sequence
<220> FEATURE:
<223> OTHER INFORMATION: Primer

<400> SEQUENCE: 62
agtgaattgg taagaccaat tagcggtacc ctcgagaaaa ggag                   44

<210> SEQ ID NO 63
<211> LENGTH: 44
<212> TYPE: DNA
<213> ORGANISM: Artificial sequence
<220> FEATURE:
<223> OTHER INFORMATION: Primer

<400> SEQUENCE: 63
attggtctta ccaattcact ttatatttta cataatcgcg cgct                   44

<210> SEQ ID NO 64
<211> LENGTH: 42
<212> TYPE: DNA
<213> ORGANISM: Artificial sequence
<220> FEATURE:
<223> OTHER INFORMATION: Primer

<400> SEQUENCE: 64
gtgatattgg taagaccaat agcggtaccc tcgagaaaag ga                     42

<210> SEQ ID NO 65
<211> LENGTH: 44
<212> TYPE: DNA
<213> ORGANISM: Artificial sequence
<220> FEATURE:
<223> OTHER INFORMATION: Primer

<400> SEQUENCE: 65
attggtctta ccaatatcac tttatattttt acataatcgc gcgc                  44

<210> SEQ ID NO 66
<211> LENGTH: 41
<212> TYPE: DNA
<213> ORGANISM: Artificial sequence
<220> FEATURE:
<223> OTHER INFORMATION: Primer

<400> SEQUENCE: 66
tgataattgg taagaccaat gcggtaccct cgagaaaagg a                      41

<210> SEQ ID NO 67
<211> LENGTH: 47
<212> TYPE: DNA
<213> ORGANISM: Artificial sequence
<220> FEATURE:
<223> OTHER INFORMATION: Primer

<400> SEQUENCE: 67
```
attggtctta ccaattatca ctttatattt tacataatcg cgcgctt        47

<210> SEQ ID NO 68
<211> LENGTH: 42
<212> TYPE: DNA
<213> ORGANISM: Artificial sequence
<220> FEATURE:
<223> OTHER INFORMATION: Primer

<400> SEQUENCE: 68
gatagattgg taagaccaat cggtaccctc gagaaaagga gg        42

<210> SEQ ID NO 69
<211> LENGTH: 46
<212> TYPE: DNA
<213> ORGANISM: Artificial sequence
<220> FEATURE:
<223> OTHER INFORMATION: Primer

<400> SEQUENCE: 69
attggtctta ccaatctatc actttatatt ttacataatc gcgcgc        46

<210> SEQ ID NO 70
<211> LENGTH: 43
<212> TYPE: DNA
<213> ORGANISM: Artificial sequence
<220> FEATURE:
<223> OTHER INFORMATION: Primer

<400> SEQUENCE: 70
atagcattgg taagaccaat ggtaccctcg agaaaaggag gaa        43

<210> SEQ ID NO 71
<211> LENGTH: 46
<212> TYPE: DNA
<213> ORGANISM: Artificial sequence
<220> FEATURE:
<223> OTHER INFORMATION: Primer

<400> SEQUENCE: 71
attggtctta ccaatgctat cactttatat tttacataat cgcgcg        46

<210> SEQ ID NO 72
<211> LENGTH: 44
<212> TYPE: DNA
<213> ORGANISM: Artificial sequence
<220> FEATURE:
<223> OTHER INFORMATION: Primer

<400> SEQUENCE: 72
tagcgattgg taagaccaat gtaccctcga gaaaaggagg aaaa        44

<210> SEQ ID NO 73
<211> LENGTH: 46
<212> TYPE: DNA
<213> ORGANISM: Artificial sequence
<220> FEATURE:
<223> OTHER INFORMATION: Primer

<400> SEQUENCE: 73
attggtctta ccaatcgcta tcactttata ttttacataa tcgcgc        46

<210> SEQ ID NO 74
<211> LENGTH: 49
<212> TYPE: DNA

<213> ORGANISM: Artificial sequence
<220> FEATURE:
<223> OTHER INFORMATION: Primer

<400> SEQUENCE: 74
agcggattgg taagaccaat taccctcgag aaaaggagga aaaaaaatg         49

<210> SEQ ID NO 75
<211> LENGTH: 47
<212> TYPE: DNA
<213> ORGANISM: Artificial sequence
<220> FEATURE:
<223> OTHER INFORMATION: Primer

<400> SEQUENCE: 75
attggtctta ccaatccgct atcactttat attttacata atcgcgc         47

<210> SEQ ID NO 76
<211> LENGTH: 27
<212> TYPE: DNA
<213> ORGANISM: Artificial sequence
<220> FEATURE:
<223> OTHER INFORMATION: Primer

<400> SEQUENCE: 76
atgggtaagg gagaagaact tttcact                               27

<210> SEQ ID NO 77
<211> LENGTH: 24
<212> TYPE: DNA
<213> ORGANISM: Artificial sequence
<220> FEATURE:
<223> OTHER INFORMATION: Primer

<400> SEQUENCE: 77
accacctatc aggatccagt tgca                                  24

<210> SEQ ID NO 78
<211> LENGTH: 49
<212> TYPE: DNA
<213> ORGANISM: Artificial sequence
<220> FEATURE:
<223> OTHER INFORMATION: Primer

<400> SEQUENCE: 78
gtgcaactgg atcctgatag gtggtggttc acaacggtaa atccatgct       49

<210> SEQ ID NO 79
<211> LENGTH: 56
<212> TYPE: DNA
<213> ORGANISM: Artificial sequence
<220> FEATURE:
<223> OTHER INFORMATION: Primer

<400> SEQUENCE: 79
tgaaaagttc ttctcccctta cccattttttt ctcctccttt ttcctaaact ctctca    56

<210> SEQ ID NO 80
<211> LENGTH: 47
<212> TYPE: DNA
<213> ORGANISM: Artificial sequence
<220> FEATURE:
<223> OTHER INFORMATION: Primer

<400> SEQUENCE: 80
gtgcaactgg atcctgatag gtggtttccc caaaatcgga gcaagcg         47

<210> SEQ ID NO 81
<211> LENGTH: 53
<212> TYPE: DNA
<213> ORGANISM: Artificial sequence
<220> FEATURE:
<223> OTHER INFORMATION: Primer

<400> SEQUENCE: 81
tgaaaagttc ttctccctta cccatgatct ttctcctcca tcgattgttg tct        53

<210> SEQ ID NO 82
<211> LENGTH: 49
<212> TYPE: DNA
<213> ORGANISM: Artificial sequence
<220> FEATURE:
<223> OTHER INFORMATION: Primer

<400> SEQUENCE: 82
gtgcaactgg atcctgatag gtggttatcc ctaaccgtat ggaacaggc              49

<210> SEQ ID NO 83
<211> LENGTH: 53
<212> TYPE: DNA
<213> ORGANISM: Artificial sequence
<220> FEATURE:
<223> OTHER INFORMATION: Primer

<400> SEQUENCE: 83
tgaaaagttc ttctccctta cccatacaaa aagaaccccc tttcatctca tat        53

<210> SEQ ID NO 84
<211> LENGTH: 48
<212> TYPE: DNA
<213> ORGANISM: Artificial sequence
<220> FEATURE:
<223> OTHER INFORMATION: Primer

<400> SEQUENCE: 84
atgtttcaat tggtcttacc aatcttcatg agaaagctcc ggcttaac               48

<210> SEQ ID NO 85
<211> LENGTH: 57
<212> TYPE: DNA
<213> ORGANISM: Artificial sequence
<220> FEATURE:
<223> OTHER INFORMATION: Primer

<400> SEQUENCE: 85
ggtaagacca attgaaacat ttttcatatt gaatcgtata atgagagagt ttaggaa     57

<210> SEQ ID NO 86
<211> LENGTH: 49
<212> TYPE: DNA
<213> ORGANISM: Artificial sequence
<220> FEATURE:
<223> OTHER INFORMATION: Primer

<400> SEQUENCE: 86
gtataattgg taagaccaat atgagagagt ttaggaaaaa ggaggagaa              49

<210> SEQ ID NO 87
<211> LENGTH: 57
<212> TYPE: DNA
<213> ORGANISM: Artificial sequence
<220> FEATURE:

<223> OTHER INFORMATION: Primer

<400> SEQUENCE: 87
attggtctta ccaattatac gattcaatat gaaaaatgtt tcacttcatg agaaagc        57

<210> SEQ ID NO 88
<211> LENGTH: 50
<212> TYPE: DNA
<213> ORGANISM: Artificial sequence
<220> FEATURE:
<223> OTHER INFORMATION: Primer

<400> SEQUENCE: 88
gagagattgg taagaccaat agtttaggaa aaaggaggag aaaaaatggg        50

<210> SEQ ID NO 89
<211> LENGTH: 52
<212> TYPE: DNA
<213> ORGANISM: Artificial sequence
<220> FEATURE:
<223> OTHER INFORMATION: Primer

<400> SEQUENCE: 89
attggtctta ccaatctctc attatacgat tcaatatgaa aaatgtttca ct        52

<210> SEQ ID NO 90
<211> LENGTH: 45
<212> TYPE: DNA
<213> ORGANISM: Artificial sequence
<220> FEATURE:
<223> OTHER INFORMATION: Primer

<400> SEQUENCE: 90
aaaatattgg taagaccaat aggtttacga cttgtcagct ttggg        45

<210> SEQ ID NO 91
<211> LENGTH: 44
<212> TYPE: DNA
<213> ORGANISM: Artificial sequence
<220> FEATURE:
<223> OTHER INFORMATION: Primer

<400> SEQUENCE: 91
attggtctta ccaatatttt tgcacattta tgacttccat tgca        44

<210> SEQ ID NO 92
<211> LENGTH: 46
<212> TYPE: DNA
<213> ORGANISM: Artificial sequence
<220> FEATURE:
<223> OTHER INFORMATION: Primer

<400> SEQUENCE: 92
attggtaaga ccaatttagg ctatataaga caacaatcga tggagg        46

<210> SEQ ID NO 93
<211> LENGTH: 46
<212> TYPE: DNA
<213> ORGANISM: Artificial sequence
<220> FEATURE:
<223> OTHER INFORMATION: Primer

<400> SEQUENCE: 93
cctaaattgg tcttaccaat gttcccaaag ctgacaagtc gtaaac        46

```
<210> SEQ ID NO 94
<211> LENGTH: 46
<212> TYPE: DNA
<213> ORGANISM: Artificial sequence
<220> FEATURE:
<223> OTHER INFORMATION: Primer

<400> SEQUENCE: 94
tatatattgg taagaccaat aagacaacaa tcgatggagg agaaag          46

<210> SEQ ID NO 95
<211> LENGTH: 42
<212> TYPE: DNA
<213> ORGANISM: Artificial sequence
<220> FEATURE:
<223> OTHER INFORMATION: Primer

<400> SEQUENCE: 95
attggtctta ccaatatata gcctaagttc ccaaagctga ca              42

<210> SEQ ID NO 96
<211> LENGTH: 43
<212> TYPE: DNA
<213> ORGANISM: Artificial sequence
<220> FEATURE:
<223> OTHER INFORMATION: Primer

<400> SEQUENCE: 96
tttgaaagga ggttctaaca ctttaatttt tacgggccgg gcg             43

<210> SEQ ID NO 97
<211> LENGTH: 33
<212> TYPE: DNA
<213> ORGANISM: Artificial sequence
<220> FEATURE:
<223> OTHER INFORMATION: Primer

<400> SEQUENCE: 97
tgttagaacc tcctttcaaa tcatacatat gag                        33

<210> SEQ ID NO 98
<211> LENGTH: 49
<212> TYPE: DNA
<213> ORGANISM: Artificial sequence
<220> FEATURE:
<223> OTHER INFORMATION: Primer

<400> SEQUENCE: 98
acataattgg taagaccaat tgagatgaaa ggggttctt tttgtatgg         49

<210> SEQ ID NO 99
<211> LENGTH: 48
<212> TYPE: DNA
<213> ORGANISM: Artificial sequence
<220> FEATURE:
<223> OTHER INFORMATION: Primer

<400> SEQUENCE: 99
attggtctta ccaattatgt atgatttgaa aggaggttct aacactttt        48

<210> SEQ ID NO 100
<211> LENGTH: 47
<212> TYPE: DNA
<213> ORGANISM: Artificial sequence
<220> FEATURE:
<223> OTHER INFORMATION: Primer
```

```
<400> SEQUENCE: 100
gatgaattgg taagaccaat aaggggttc tttttgtatg ggtaagg         47

<210> SEQ ID NO 101
<211> LENGTH: 48
<212> TYPE: DNA
<213> ORGANISM: Artificial sequence
<220> FEATURE:
<223> OTHER INFORMATION: Primer

<400> SEQUENCE: 101
attggtctta ccaattcatc tcatatgtat gatttgaaag gaggttct        48
```